(12) United States Patent
Höger et al.

(10) Patent No.: US 6,486,162 B2
(45) Date of Patent: Nov. 26, 2002

(54) 2-{3-[4-(2-T-BUTYL-6-TRIFLUOROMETHYL-4-PYRIMIDINYL)-1- PIPERAZINYL] PROPYLTHIO}-4-PYRIMIDINOL FUMARATE

(75) Inventors: Thomas Höger, Edingen-Neckarhausen (DE); Dorothea Starck, Ludwigshafen (DE); Hans-Jorg Treiber, Bruhl (DE); Stefan Koser, Ludwigshafen (DE); Bernd Schaefer, Dierbach (DE); Marco Thyes, Ludwigshafen (DE); Stefan Blank, Singapore (SG)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/039,974

(22) Filed: Jan. 8, 2002

(65) Prior Publication Data

US 2002/0143179 A1 Oct. 3, 2002

Related U.S. Application Data

(63) Continuation-in-part of application No. 09/485,460, filed as application No. PCT/EP98/05178 on Aug. 14, 1998, now abandoned.

(30) Foreign Application Priority Data

Aug. 14, 1997 (DE) .......................... 197 35 410

(51) Int. Cl.$^7$ ..................... A61K 31/506; C07D 403/14
(52) U.S. Cl. ................... 514/252.14; 544/296
(58) Field of Search ...................... 544/296; 514/252.14

(56) References Cited

FOREIGN PATENT DOCUMENTS

WO        WO 96/02519 A1      2/1996

OTHER PUBLICATIONS

Lammers et al., Molecular Psychiatry,5, pp. 378–388 (2000).*

Reynolds et al., *Drugs*, vol. 51, p. 7–11, 1996.

* cited by examiner

*Primary Examiner*—Emily Bernhardt
(74) *Attorney, Agent, or Firm*—Keil & Weinkauf

(57) ABSTRACT

The fumaric acid salt of 2-{3-[4-(2-t-butyl-6-trifluoromethyl-4-pyrimidinyl)-1-piperazinyl]propylthio}-4-pyrimidinol is useful for treating disorders which respond to dopamine $D_3$ ligands. It has higher stability at low pH and is therefore particularly suitable for oral administration in pharmaceutical compositions comprising this salt.

7 Claims, No Drawings

2-{3-[4-(2-T-BUTYL-6-TRIFLUOROMETHYL-4-PYRIMIDINYL)-1-PIPERAZINYL]PROPYLTHIO}-4-PYRIMIDINOL FUMARATE

This is a continuation-in-part of application Ser. No. 09/485,460, filed on Feb. 10, 2000, now abandoned which is a national stage application of PCT/EP 98/05178, filed on Aug. 14, 1998.

The invention relates to the fumaric acid salt of 2-{3-[4-(2-t-butyl-6-trifluoromethyl-4-pyrimidinyl)-1-piperazinyl]propylthio}-4-pyrimidinol and to a pharmaceutical composition comprising this compound. This compound has valuable therapeutic properties and is particularly useful for treating disorders which respond to dopamine $D_3$ ligands.

WO 96/02519 describes said compound in the form of the free base of the formula

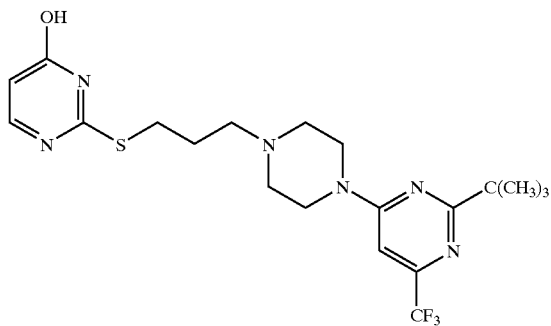

which is likewise useful for treating disorders which respond to dopamine $D_3$ ligands. However, a salt of this compound is not disclosed.

It has now been found, surprisingly, that the acid addition salt of this compound with fumaric acid has particular advantages.

The present invention therefore relates to the fumaric acid salt of 2-{3-[4-(2-t-butyl-6-trifluoromethyl-4-pyrimidinyl)-1-piperazinyl]propylthio}-4-pyrimidinol and to a pharmaceutical composition comprising this compound.

The present invention also relates to tautomeric forms (pyridone structure) as well as solvates and hydrates of the fumaric acid salt.

The fumaric acid salt has very good affinity and high selectivity for the $D_3$ receptor, i.e. it is a selective dopamine $D_3$receptor ligand which acts regioselectively in the limbic system. It has a selectivity, $K_i\ D_2/K_i\ D_3$ of 120 (cf. WO 96/02519). The compound is therefore useful for treating disorders which respond to dopamine $D_3$ligands, eg. for treating disorders of the central nervous system, in particular schizophrenia, depressions, neuroses and psychoses. It is additionally useful for treating sleep disturbances and nausea and as antihistamine. Solubility tests of the substances showed a substantially higher solubility of the salt in water compared to that of the free base. Thus, resorption is significantly enhanced when the substance is administered orally and especially parenterally.

Furthermore, the fumarate is more soluble in polar solvents such as $C_1$–$C_6$-alkanols than the free base. Because of the altered solubility characteristics, it can also be purified more simply while avoiding physiologically unacceptable solvents. Additionally, the fumaric acid salt of 2-{3-[4-(2-t-butyl-6-trifluoromethyl-4-pyrimidinyl)-1-piperazinyl]propylthio}-4-pyrimidinol exhibits a higher stability against oxidative processes than 2-{3-[4-(2-t-butyl-6-trifluoromethyl-4-pyrimidinyl)-1-piperazinyl]propylthio}-4-pyrimidinol.

The free base can be prepared by the general processes described in WO 96/02519, preferably by process (ii). The fumarate is obtainable by reacting the free base with fumaric acid in a suitable solvent such as $C_1$–$C_6$-alkanols, in particular methanol, ethanol, n-propanol, isopropanol and n-butanol, a mixture of water and one of the said alcohols, or an ester such as ethyl acetate. An elevated temperature will generally be used so that the required fumarate crystallizes out on cooling and can be isolated in a straightforward manner. The fumaric acid is generally added in equimolar amounts or with a slight excess of up to about 10%. The fumarate produced in this way already has high purity. It can also be additionally purified by stirring in or recrystallization from a suitable solvent, e.g. water, one of the abovementioned alkanols, esters or mixtures thereof.

For treating the abovementioned disorders, the novel compound is administered orally or parenterally (subcutaneously, intravenously, intramuscularly, intraperitoneally) in a conventional way. Oral administration is preferred.

The dosage depends on the age, condition and weight of the patient and on the mode of administration. As a rule, the daily dose of active substance is about 10 to 1000 mg per patient and day on oral administration and about 1 to 500 mg per patient and day on parenteral administration.

The invention also relates to pharmaceutical compositions comprising the novel compound. These compositions are in the form of the usual solid or liquid pharmaceutical forms, for example as uncoated or (film-)coated tablets, capsules, powders, granules, suppositories, solutions or sprays. The active substances can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al., Pharmazeutische Technologie, Thieme-Verlag, Stuttgart, 1978). The administration forms obtained in this way normally contain from 1 to 99% by weight of active substance.

The following examples serve to illustrate the invention without restricting it.

EXAMPLE 1

Preparation of the Fumaric Acid Salt of 2-{3-[4-(2-t-Butyl-6-trifluoromethyl-4-pyrimidinyl)-1-piperazinyl]propylthio]-4-pyrimidinol 2-t-Butyl-4-hydroxy-6-trifluoromethylpyrimidine(1)

The starting materials are known from the literature.

To 50 g (0.37 mol) of 2,2-dimethylpropionamidine hydrochloride, dissolved in 200 ml of ethanol, were added, at room temperature, 66.6 g (0.37 mol) of sodium methoxide (30% strength in methanol) and, after a further 30 minutes, 52 g (0.28 mol) of ethyl trifluoroacetate. After refluxing for 17 hours, the solvent was removed under reduced pressure, 200 ml of water were added to the residue and, after acidification to pH 4, the crystallized solid was isolated by filtration.

Yield: 62.2 g (98% of theory); $C_9H_{11}F_3N_2O$ (MW 220) m.p. 187–188° C.

2-t-Butyl-4-chloro-6-trifluoromethylpyrimidine (2)

Firstly 86.5 ml of thionyl chloride and then 8 ml of DMF were added dropwise to a solution of 60 g (0.27 mol) of 2-t-butyl-4-hydroxy-6-trifluoromethylpyrimidine in 800 ml of dichloromethane, and then the mixture was refluxed. The volatile constituents were removed under reduced pressure, the residue was taken up in 100 ml of dichloromethane, the pH was adjusted to 7 with saturated $NaHCO_3$ solution and, after workup by extraction, 67 g (96%) of a clear oil were obtained.

Yield 67 g (96% of theory); $C_9H_{10}ClF_3N_2$ (MW 239).

2-t-Butyl-4-(1-piperazinyl)-6-trifluoromethylpyrimidine (3)

A solution of 60 g (0.25 mol) of the chloropyrimidine described above in 200 ml of ethanol was added dropwise to a boiling solution of 129 g (1.5 mol) of piperazine in 500 ml of ethanol over the course of 2 h, and then the mixture was boiled for a further 6 h. After the reaction was complete, the solvent was removed under reduced pressure, and the residue was mixed with 2 l of water. The product crystallized on cooling and was then filtered off with suction.

Yield: 56 g (77% of theory); $C_{13}H_{19}ClF_3N_4$ (MW 288) m.p. 78–80° C.; $^1$H-NMR (250 MHZ, $CDCl_3$): d=1.3 (s, 9H); 1.8 (s, 1H); 3.0 (m, 4H); 4.7 (m, 4H); 6.6 (s, 1H) ppm.

2-t-Butyl-4-[4-(3-chloropropyl)-1-piperazinyl]-6-trifluoromethyl-pyrimidine (4)

43.2 g (0.15 mol) of the piperazine described above, dissolved in 130 ml of THF, were added dropwise to a boiling mixture of 35.1 g (0.22 mol) of 1-bromo-3-chloropropane and 16.0 g (0.16 mol) of triethylamine in 90 ml of THF, and the mixture was stirred at this temperature for 8 hours. After cooling to 4° C., the inorganic salts were filtered off, the THF phase was concentrated under reduced pressure, and the residue was recrystallized from isopropanol.

Yield: 32.1 g (61% of theory); $C_{16}H_{24}ClF_3N_4$ (MW 365) m.p. 83–84° C.; $^1$H-NMR (250 MHZ, $CDCl_3$): d=1.3 (s, 9H); 1.9 (q, 2H); 2.5 (m, 6H); 3.7 (t, 2H); 3.8 (m, 4H); 6.6 (s, 1H) ppm.

2-{3-[4-(2-t-Butyl-6-trifluoromethyl-4-pyrimidinyl)-1-35 piperazinyl]propylthio}-4-pyrimidinol (5)

8.4 g (0.066 mol) of thiouracil, 1.6 g (0.066 mol) of lithium hydroxide and 1.0 g (0.066 mol) of sodium iodide were dissolved in 200 ml of DMF and heated to 100° C. At this temperature, 20.1 g (0.055 mol) of the chlorine base described above, dissolved in 50 ml of DMF, were added, followed by stirring at 100° C. for 30 min. Then 300 ml of sodium chloride solution were added and the mixture was extracted twice with 200 ml of ethyl acetate. The organic phase was dried with sodium sulfate and, after filtration, evaporated under reduced pressure.

The residue was purified by column chromatography (silica gel, dichloromethane with 1–4% methanol).

Yield: 18 g (72% of theory). $C_{20}H_{27}F_3N_6OS$ (MW 457) m.p. 138–140° C.; $^1$H-NMR (270 MHZ, DMSO-$d_6$): d=1.3 (s, 9H); 1.8 (q, 2H); 2.4 (m, 6H); 3.3 (t, 2H); 3.75 (m, 4 H); 6.1 (d, 2H); 7.1 (s, 1H); 7.9 (2, 2H) ppm.

Preparation of the fumarate (6):

4.56 g (0.01 mol) of the base described above were dissolved in 25 ml of hot isopropanol, and a hot solution of 1.16 g (0.01 mol) of fumaric acid in 15 ml of isopropanol was added. The substance crystallized out on cooling and was filtered off, resulting in 4.4 g of the title compound as colorless crystals.

Yield: 4.4 g (76% of theory); $C_{20}H_{27}F_3N_6OS \times C_4H_4O_4$ (MW 573) m.p. 200–202° C.; $^1$H-NMR (250 MHZ, DMSO-$d_6$): d=1.3 (s, 9H); 1.9 (q, 2H); 2.5 (m, 6H); 3.2 (t, 2H); 3.8 (mbr, 6H); 6.2 (d, 2H); 6.7 (s, 2H); 7.1 (s, 1H); 7.9 (d, 2H).

EXAMPLE 2

Evaluation of various acid addition salts of 2-{3-[4-(2-t-butyl-6-trifluoromethyl-4-pyrimidyl)-1-piperazinyl)propylthio}-4-5 pyrimidinol

| Acid Addition Salt | Observation |
| --- | --- |
| Hydrochloride | the aqueous solution is highly acidic; the compound is instable in the acidic medium |
| Methane sulfonate | highly hygroscopic; the crystals are deliquescent and dissolve within 3 h |
| Lactate | the acid addition salt could not be precipitated even with variation of the solvent |
| Citrate | the acid addition salt could not be precipitated even with variation of the solvent |
| Tartrate | the acid addition salt could not be precipitated even with variation of the solvent |
| Malate | precipitates slowly overnight as a very fine crystalline precipitate which is difficult to isolate and difficult to handle |
| Fumarate | non-hygroscopic salt with definite melting point; easy to handle |

The above results show that the fumaric acid salt has unique advantages in preparation and stability over these other acid addition salts.

We claim:

1. The fumaric acid salt of 2-{3-[4-(2-t-butyl-6-trifluoromethyl-4-pyrimidinyl)-1-piperazinyl]propylthio}-4-pyrimidinol of formula

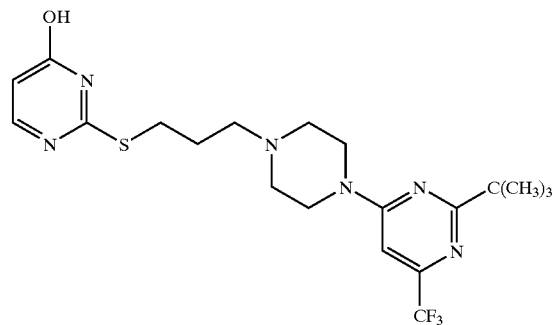

or a tautomeric form or a hydrate thereof.

2. A pharmaceutical composition comprising the fumaric acid salt or the tautomeric form or the hydrate thereof defined in claim 1, and a physiologically acceptable vehicles or ancillary substance.

3. A method for treating a disorder of the central nervous system which responds to dopamine $D_3$ ligands and is selected from the group of schizophrenia, depression, neuroses and psychoses, which method comprises administering an effective amount of the fumaric acid salt or of the tautomeric form or of the hydrate thereof defined in claim 1.

4. The method of claim 3, wherein the fumaric acid salt or the tautomeric form or the hydrate thereof is administered orally.

5. The method of claim 4, wherein the fumaric acid salt or the tautomeric form or the hydrate thereof is administered in an amount of from about 10 to 1000 mg per day.

6. The method of claim 3, wherein the fumaric acid salt or the tautomeric form or the hydrate thereof is administered parenterally.

7. The method of claim 6, wherein the fumaric acid salt or the tautomeric form or the hydrate thereof is administered in an amount from about 1 to 500 mg per day.

\* \* \* \* \*